(12) United States Patent
Sackeyfio et al.

(10) Patent No.: US 6,955,815 B2
(45) Date of Patent: Oct. 18, 2005

(54) COMBINATIONS FOR THE TREATMENT OF INFLAMMATORY DISORDERS

(75) Inventors: Robyn Sackeyfio, Ann Arbor, MI (US); Jason Fong, Philadelphia, PA (US); Nicole Hurst, Boston, MA (US); Palaniyandi Manivasakam, Brighton, MA (US); Edward Roydon Jost-Price, West Roxbury, MA (US); Grant Zimmermann, Somerville, MA (US); Curtis Keith, Boston, MA (US); Alexis Borisy, Boston, MA (US)

(73) Assignee: CombinatoRx, Incorporated, Boston, MA (US)

(*) Notice: Subject to any disclaimer, the term of this patent is extended or adjusted under 35 U.S.C. 154(b) by 0 days.

(21) Appl. No.: 10/674,744

(22) Filed: Sep. 29, 2003

(65) Prior Publication Data

US 2004/0116395 A1 Jun. 17, 2004

Related U.S. Application Data

(63) Continuation of application No. 10/191,149, filed on Jul. 9, 2002.
(60) Provisional application No. 60/304,089, filed on Jul. 9, 2001.

(51) Int. Cl.[7] ................................................ A61K 9/00
(52) U.S. Cl. ...................... 424/400; 424/430; 424/439; 424/451; 424/464; 424/489; 514/169
(58) Field of Search .............................. 424/400, 439, 424/464, 489, 430, 436, 451; 514/169

(56) References Cited

U.S. PATENT DOCUMENTS

| | | | |
|---|---|---|---|
| 4,034,087 A | 7/1977 | Voorhees | |
| 4,107,306 A | 8/1978 | Voorhees | |
| 5,900,249 A | * 5/1999 | Smith | ......................... 424/443 |
| 6,140,337 A | 10/2000 | Binder et al. | |
| 6,472,401 B2 | 10/2002 | Kreutner | |
| 6,677,326 B2 | 1/2004 | Bardsley | |

FOREIGN PATENT DOCUMENTS

WO          99/59598        11/1999

OTHER PUBLICATIONS

Allan et al., "Anti-emetic Efficacy of Dexamtheasone in Combination of Out-Patients Receiving Cytotoxic Chemotherapy," Cancer Chemotherapy and Pharmacology 18:86–87 1986.
Bonuccelli et al., "Amitriptyline and Dexamethasone Combined Treatment in Drug-Induced Headache," Cephalalgia 197–200 (1996).
Dessein et al., "Oral Low-Dose Glucocorticosteroids as Compared with Intravenous Methylprednisolone Pulses in the Treatment of Rheumatoid Arthritis," Letters to the Editor 1304–1305 (1999).
Drake et al., "Pharmacokinetics of Doxepin in Subjects with Pruritic Atopic Dermatitis," J. Am. Acad. Dermatol. 41:209–214 (1999).
Pfeiffer, R., "Drugs for Pain in the Elderly," Geriatrics 37:67–74 (1982).
Ash et al., "The Effects of Dothiepin on Subjects with Rheumatoid Arthritis and Depression," Rheumatology 38:959–967 (1999).
Barden, "Regulation of Corticosteroid Receptor Gene Expression in Depression and Antidepressant Action," Journal of Psychiatry and Neuroscience 24:25–39 (1999).
Berberian et al., "The Addition of Topical Doxepin to Corticosteroid Therapy: An Improved Treatment Regimen for Atopic Dermatitis," International Journal of Dermatology 38:145–148 (1999).
Bird and Broggini, "Paroxetine Versus Amitriptyline for Treatment of Depression Associated with Rheumatoid Arthritis: A Randomized, Double Blind, Parallel Group Study," The Journal of Rheumatology 2791–2797 (2000).
Bresnihan, "Treatment of Rheumatoid Arthritis with Interleukin 1 Receptor Antagonist," Annals of Rheumatoid Disorders 58:196–198 (1999).
Budziszewska et al., "Antidepressant Drugs Inhibit Glucocorticoid Receptor–Mediated Gene Transcription– A Possible Mechanism," British Journal of Pharmacology 130:1385–1393 (2000).
Calvo et al., "Pharmacokinetics of Amoxapine and its Active Metabolites," International Journal of Clinical Pharmacology, Therapy and Toxicology 23:180–185 (1985).
Carty et al., "The Biochemistry and Pharmacology of TNFα and β, Apr. 21, 1995, New York," Inflammation Research 44:455–457 (1995).
Chuck et al., "The Effects of Dothiepin on Subjects with Rheumatoid Arthritis and Depression," Rheumatology 39:1425–1427 (2000).
Clark, "Chronic Pain, Depression, and Antidepressants: Issues and Relationships," Johns Hopkins Arthritis Website: http://www.hopkins–arthritis.som.ihmi.edu/mngmnt/depression.html, Oct. 4, 2002.
Coupet et al., "The Effects of 2–chloro–11–(4–methyl–I–piperazinyl)–dibenz[b,f] [1,4]oxazepine (loxapine) and its Derivatives on the Dopamine– Sensitive Adenylate Cyclase of Rat Striatal Homogenates," Brain Research 116:177–180 (1976).
Didonato et al., "Molecular Mechanisms of Immunosuppression and Anti–Inflammatory Activities by Glucocorticoids," American Journal of Respiratory and Critical Care Medicine 154:S11–S15 (1996).

(Continued)

Primary Examiner—Shelley A. Dodson
Assistant Examiner—Konata M. George
(74) Attorney, Agent, or Firm—Clark & Elbing LLP

(57) ABSTRACT

The invention features a pharmaceutical composition that includes amoxapine and a corticosteroid.

8 Claims, No Drawings

OTHER PUBLICATIONS

Ehrenstein, "Combination Therapy in Rheumatoid Arthritis," *British Journal of Rheumatology* 34:580–581 (1995).

Fishbain, "Evidence–based Data on Pain Relief with Antidepressants," *Annals of Medicine* 32:305–316 (2000).

Fowler et al., "Imipramine, Rheumatoid Arthritis and Rheumatoid Factor," *Current Medical Research and Opinion* 5:241–246 (1977).

Frank et al., "Antidepressant Analgesia in Rheumatoid Arthritis," *The Journal of Rheumatology* 15:1632–1638 (1988).

Godefroy et al., "Do Acute or Chronic Tricyclic Antidepressants Modify Morphine Antinociception In Arthritic Rats?" *Pain* 25:233–244 (1986).

Gupta et al., "Antidepressant Drugs in Dermatology," *Archives of Dermatology* 123:647–652 (1987).

Gupta and Gupta, "The use of Antidepressant Drugs in Dermatology," *Journal of European Academy of Dermatology and Venereology* 15:512–518 (2001).

Healey and Wilske, "Evaluating Combination Drug Therapy in Rheumatoid Arthritis," *Journal of Rheumatology* 18:641–642 (1991).

Hinze–Selch et al., "Effects of Antidepressants on Weight and on the Plasma Levels of Leptin, TNF–$\alpha$ and Soluble TNF Receptors: A Longitudinal Study in Patients Treated with Amitriptyline or Paroxetine," *Neuropsychopharmacology* 23:13–19 (2000).

Holsboer, "The Corticosteroid Receptor Hypothesis of Depression," *Neuropsychopharmacology* 23:477–501 (2000).

Jue et al., "Amoxapine: A Review of its Pharmacology and Efficacy in Depressed States," *Drugs* 24:1–23 (1982).

Kirwan, "Systemic Low–dose Glucocorticoid Treatment in Rheumatoid Arthritis," *Rheumatoid Arthritis* 27:389–403 (2001).

Koh et al., "Low Dose Amitriptyline in Ankylosing Spondylitis: A Short Term, Double Blind, Placebo Controlled Study," *The Journal of Rheumatology* 24:2158–2161 (1997).

Kristensen, "Plasma Protein Binding of Imipramine in Patients with Rheumatoid Arthritis," *European Journal of Clinical Pharmacology* 28:693–696 (1985).

Kubera et al., "Effect of Repeated Desipramine and Fluoxetine Administration on Post–Adjuvant Arthritis," *Polish Journal of Pharmacology* 52:229–235 (2000).

Lanquillon et al., "Cytokine Production and Treatment Response in Major Depressive Disorder," *Neuropsychopharmacology* 22:370–379 (2000).

Lee et al., "Effect of Steroids on the Inhibition of Platelet 5HT Uptake by Desipramine and Other Antidepressants," *European Journal of Pharmacology* 106:255–262 (1985).

Lydiard et al., "Amoxapine—An Antidepressant with Some Neuroleptic Properties? A Review of Its Chemistry, Animal Pharmacology and Toxicology, Human Pharmacology, and Clinical Efficacy," *Pharmacotherapy* 1:163–178 (1981).

MacFarlane et al., "Trimipramine in Rheumatoid Arthritis: A Randomized Double–Blind Trial in Relieving Pain and Joint Tenderness," *Current Medical Research and Opinion* 10:89–93 (1986).

MacNeill et al., "Imipramine and Rheumatoid Factor," *Journal of International Medical Research* 4:23–27 (1976).

Maes et al., "Negative Immunoregulatory Effects of Antidepressants: Inhibition of Interferon–$\gamma$ and Stimulation of Interleukin–10 Secretion," *Neuropsychopharmacology* 20:370–379 (1999).

Maes, "Major Depression and Activation of the Inflammatory Response System," *Advances in Experimental Medicine and Biology* 461:25–46 (1999).

Maes et al., "Effects of Atypical Antipsychotics on the Inflammatory Response System in Schizophrenic Patients Resistant to Treatment with Typical Neuroleptics," *European Neuropsychopharmacology* 10:119–124 (2000).

Magni, "The Use of Antidepressants in the Treatment of Chronic Pain," *Drugs* 42:730–748 (1991).

Martelli et al., "Mechanism of Inhibition of Experimental Inflammation by Antidepressant Drugs," *European Journal of Pharmacology* 2:229–233 (1967).

Mastaglia, "Adverse Effects of Drugs on Muscle," *Drugs* 24:304–321 (1982).

McBride et al., "Management of Rheumatoid Arthritis," *Southern Medical Journal* 307–314 (1969).

McLain, "Rheumatoid Arthritis—Update on New Therapies," *Southern Medical Journal* 94:893–895 (2001).

Michelson et al., "Imipramine Reduces the Local Inflammatory Response to Carrageenin," *Agents Actions* 42:25–28 (1994).

Morris, "Combination Drug Therapy in Rheumatoid Arthritis," *The Journal of Rheumatology* 23:1113 (1996).

Okugawa et al., "Long–Term Treatment with Antidepressants Increases Glucocorticoid Receptor Binding and Gene Expression in Cultured Rat Hippocampal Neurones," *Journal of Neuroendocrinology* 11:887–895 (1999).

Pariante et al., "Steroid–Independent Translocation of the Glucocorticoid Receptor by the Antidepressant Desipramine," *Molecular Pharmacology* 52:571–581 (1997).

Petitto et al., "Improvement of Arthritis with Fluoxetine," *Psychosomatics* 338–341.

Pullar, "Combination Therapy in Rheumatoid Arthritis," *British Journal of Rheumatology* 30:311–312 (1991).

Puttini et al., "A Comparison of Dothiepin Versus Placebo in the Treatment of Pain in Rheumatoid Arthritis and the Association of Pain with Depression," *Journal of International Medical Research* 16:331–337 (1988).

Russell et al., "Combination Drug Therapy in Rheumatoid Arthritis," *The Journal of Rheumatology* 24:803–804 (1997).

Scott et al., "Use of Transdermal Amitriptyline Gel in a Patient with Chronic Pain and Depression," *Pharmacotherapy* 19:236–239 (1999).

Swinson, "Antidepressant Therapy and Rheumatoid Arthritis," *The Journal of Rheumatology* 17:277 (1990).

Tangri et al., "Anti–Inflammatory Activity of Imipramine and Congeners," *Biochemical Pharmacology* 15:825–831 (1966).

Tasset and Pesce, "Amoxapine in Human Overdose," *Journal of Analytical Toxicology*, 8:124–128 (1984).

Thorpe and Marchant–Williams, "The Role of an Antidepressant, Dibenzepin (Noveril), in the Relief of Pain in Chronic Arthritic States," *Medical Journal of Australia* 1:264–266 (1974). Van den Berg et al., "Role of Tumour Necrosis Factor α in Experimental Arthritis: Separate Activity of Interleukin 1 β in Chronicity and Cartilage Destruction," *Annals of Rheumatoid Disorders* 58:140–148 (1999).

Vedder et al., "Regulation of Glucocorticoidreceptor–mRNA in Human Blood Cells by Amitriptyline and Dexamethasone," *Journal of Psychiatric Research* 33:303–308 (1999).

Williams, "Combination Second–Line Therapy for Rheumatoid Arthritis," *British Journal of Rheumatology* 33:603–604 (1994).

Xia et al., "Tricyclic Antidepressants Inhibit IL–6, IL–1 and TNF–α Release in Human Blood Monocytes and IL–2 and Interferon–γ in T Cells," *Immunopharmacology* 34:27–37 (1996).

Yaron et al., "Fluoxetine and Amitriptyline Inhibit Nitric Oxide, Prostaglandin $E_2$, and Hyaluronic Acid Production in Human Synovial Cells and Synovial Tissue Cultures," *Arthritis and Rheumatism* 42:2561–2568 (1999).

* cited by examiner

COMBINATIONS FOR THE TREATMENT OF INFLAMMATORY DISORDERS

CROSS-REFERENCE TO RELATED APPLICATIONS

This application is a continuation of U.S. Utility Application Ser. No. 10/191,149, filed Jul. 9, 2002, which claims the benefit of U.S. Provisional Application Ser. No. 60/304,089, filed Jul. 9, 2001, each of which is hereby incorporated by reference.

BACKGROUND OF THE INVENTION

The invention relates to the treatment of inflammatory disorders.

Inflammation occurs when tissues are injured by viruses, bacteria, trauma, chemicals, heat, cold or any other harmful stimulus. Chemicals including bradykinin, histamine, serotonin and others are released, attracting tissue macrophages and white blood cells to localize in an area to engulf and destroy foreign substances. During this process, chemical mediators such as TNFα are released, giving rise to inflammation. Inflammatory disorders are those in which the inflammation is sustained or chronic. One example of an inflammatory disorder is osteoarthritis.

Immunoinflammatory disorders (e.g., rheumatoid arthritis, psoriasis, ulcerative colitis, Crohn's disease, stroke-induced brain cell death, ankylosing spondylitis, fibromyalgia, and autoimmune diseases such as asthma, multiple sclerosis, type I diabetes, systemic lupus erythematosus, scleroderma, systemic sclerosis, and Sjögren's syndrome) are inflammatory disorders characterized by dysregulation of the immune system and inappropriate mobilization of body's defenses against its own healthy tissue.

One percent of humans world-wide are afflicted with rheumatoid arthritis, a relentless, progressive disease causing severe swelling, pain, and eventual deformity and destruction of joints. According to the Arthritis Foundation, rheumatoid arthritis currently affects over two million Americans, of which women are three times more likely to be afflicted. Rheumatoid arthritis is characterized by inflammation of the lining of the joints and/or other internal organs, and the presence of elevated numbers of lymphocytes and high levels of proinflammatory cytokines.

Treatment of rheumatoid arthritis generally includes administration of (i) non-steroidal anti-inflammatory drugs (NSAIDs; e.g., detoprofen, diclofenac, diflunisal, etodolac, fenoprofen, flurbiprofen, ibuprofen, indomethacin, ketoprofen, meclofenameate, mefenamic acid, meloxicam, nabumeone, naproxen sodium, oxaprozin, piroxicam, sulindac, tolmetin, celecoxib, rofecoxib, aspirin, choline salicylate, salsalte, and sodium and magnesium salicylate); (ii) steroids (e.g., cortisone, dexamethasone, hydrocortisone, methylprednisolone, prednisolone, prednisone, triamcinolone); (iii) DMARDs, i.e., disease modifying anti-rheumatic drugs (e.g., cyclosporine, azathioprine, methotrexate, leflunomide, cyclophosphamide, hydroxychloroquine, sulfasalazine, D-penicillamine, minocycline, and gold); or (iv) recombinant proteins (e.g., ENBREL® (etanercept, a soluble TNF receptor) and REMICADE® (infliximab) a chimeric monoclonal anti-TNF antibody).

There is a need to develop new regimens for the treatment of rheumatoid arthritis, and other inflammatory disorders.

SUMMARY OF THE INVENTION

We have discovered that the combination of amoxapine (2-cloro-11(1-piperazinyl)dibenz[b,f][1,4]oxazine) and prednisolone (also known as 1-dehydrocortisol; 1-dehydrohydrocortisone; 1,4-pregnadiene-11beta,17alpha,21-triol-3,20-dione; and 11beta,17alpha,21-trihydroxy-1,4-pregnadiene-3,20-dione) brings about substantial suppression of TNFα levels induced in peripheral blood mononuclear cells (PBMCs).

Amoxapine is a tricyclic antidepressant (TCA). Based on the ability of amoxapine to act in concert with prednisolone to inhibit TNFα levels, one skilled in the art will recognize that other TCAs can also be used in the present invention. Structural analogs of amoxapine that are not tricyclic antidepressants can also be used. Exemplary structural analogs include, for example, clothiapine, perlapine, fluperlapine, and dibenz (b,f)(1,4)oxazepine, 2-chloro-11-(4-methyl-1-piperazinyl)-, monohydrochloride.

Prednisolone is a corticosteroid. Based on the shared structural features and apparent mechanism of action among the corticosteroid family, one skilled in the art will recognize that other corticosteroids can be used in combination with amoxapine or other TCAs to treat inflammatory disorders.

Accordingly, the invention features a method for treating a patient having an inflammatory disorder, by administering to the patient (i) a TCA (e.g, amoxapine); and (ii) a corticosteroid (e.g., prednisolone) simultaneously or within 14 days of each other, in amounts sufficient to suppress TNFα levels sufficiently to produce a therapeutic benefit to the patient. In one embodiment, the two compounds are amoxapine and prednisolone.

The invention also features a method for treating a patient having an inflammatory disorder by administering to the patient (i) clothiapine, perlapine, fluperlapine, or dibenz (b,f)(1,4)oxazepine, 2-chloro-11-(4-methyl-1-piperazinyl)-, monohydrochloride; and (ii) a corticosteroid (e.g., prednisolone) simultaneously or within 14 days of each other, in amounts sufficient to suppress TNFα levels sufficiently to produce a therapeutic benefit to the patient.

Preferably, the two compounds of the invention are administered within ten days of each other, more preferably within five days of each other, and most preferably within twenty-four hours of each other, or simultaneously. The disorder treated according to the invention can be, for example, rheumatoid arthritis, psoriasis, ulcerative colitis, Crohn's disease, stroke-induced brain cell death, ankylosing spondylitis, and fibromyalgia, asthma, multiple sclerosis, type I diabetes, systemic lupus erythematosus, scleroderma, systemic sclerosis, or Sjögren's syndrome.

In the above-described treatment method, both compounds are preferably provided together in a pharmaceutical composition that also includes a pharmaceutically acceptable carrier.

The invention also features a pharmaceutical composition that includes (i) a TCA (e.g., amoxapine); and (ii) a corticosteroid (e.g., prednisolone), along with a pharmaceutically acceptable carrier, diluent, or excipient.

The invention also features a method for identifying compounds useful for treating a patient having an inflammatory disorder. The method includes the steps of: contacting immune cells in vitro with (i) a TCA or a corticosteroid; and (ii) a candidate compound, and determining whether the immune response is modulated relative to (a) immune cells contacted with the TCA or corticosteroid but not contacted with the candidate compound, and (b) immune cells contacted with the candidate compound but not with the TCA or corticosteroid. A candidate compound that, when combined with the TCA or corticosteroid, modulates the immune response to a greater degree than controls, is a compound that is potentially useful for treating a patient having an inflammatory disorder.

Compounds useful in the invention include those described herein in any of their pharmaceutically acceptable forms, including isomers such as diastereomers and enantiomers, salts, solvates, and polymorphs thereof, as well as racemic mixtures of the compounds described herein.

By "tricyclic antidepressant" or "TCA" is meant a compound having one the formulas (I), (II), or (III):

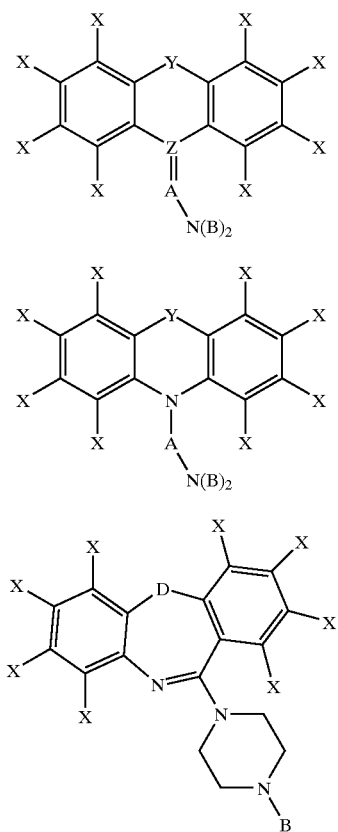

wherein each X is, independently, H, Cl, F, Br, I, $CH_3$, $CF_3$, OH, $OCH_3$, $CH_2CH_3$, or $OCH_2CH_3$; Y is $CH_2$, O, NH, $S(O)_{0-2}$, $(CH_2)_3$, $(CH)_2$, $CH_2O$, $CH_2NH$, CHN, or $CH_2S$; Z is C or S; A is a branched or unbranched, saturated or monounsaturated hydrocarbon chain having between 3 and 6 carbons, inclusive; each B is, independently, H, Cl, F, Br, I, $CX_3$, $CH_2CH_3$, $OCX_3$, or $OCX_2CX_3$; and D is $CH_2$, O, NH, $S(O)_{0-2}$.

In preferred embodiments, each X is, independently, H, Cl, or F; Y is $(CH_2)_2$, Z is C; A is $(CH_2)_3$; and each B is, independently, H, Cl, or F.

Exemplary tricyclic antidepressants include, for example, amoxapine, 8-hydroxyamoxapine, 7-hydroxyamoxapine, loxapine, loxapine succinate, loxapine hydrochloride, 8-hydroxyloxapine, amitriptyline, clopramine, doxepin, imipramine, trimipramine, desipramine, nortriptyline, and protriptyline.

By "corticosteroid" is meant any naturally occurring or synthetic steroid hormone which can be derived from cholesterol and is characterized by a hydrogenated cyclopentanoperhydrophenanthrene ring system. Naturally occurring corticosteroids are generally produced by the adrenal cortex. Synthetic corticosteroids may be halogenated. Functional groups required for activity include a double bond at Δ4, a C3 ketone, and a C20 ketone. Corticosteroids may have glucocorticoid and/or mineralocorticoid activity.

Exemplary corticosteroids include, for example, dexamethasone, betamethasone, triamcinolone, triamcinolone acetonide, triamcinolone diacetate, triamcinolone hexacetonide, beclomethasone, dipropionate, beclomethasone dipropionate monohydrate, flumethasone pivalate, diflorasone diacetate, fluocinolone acetonide, fluorometholone, fluorometholone acetate, clobetasol propionate, desoximethasone, fluoxymesterone, fluprednisolone, hydrocortisone, hydrocortisone acetate, hydrocortisone butyrate, hydrocortisone sodium phosphate, hydrocortisone sodium succinate, hydrocortisone cypionate, hydrocortisone probutate, hydrocortisone valerate, cortisone acetate, paramethasone acetate, methylprednisolone, methylprednisolone acetate, methylprednisolone sodium succinate, prednisolone, prednisolone acetate, prednisolone sodium phosphate, prednisolone tebutate, clocortolone pivalate, flucinolone, dexamethasone 21-acetate, betamethasone 17-valerate, isoflupredone, 9-fluorocortisone, 6-hydroxydexamethasone, dichlorisone, meclorisone, flupredidene, doxibetasol, halopredone, halometasone, clobetasone, diflucortolone, isoflupredone acetate, fluorohydroxyandrostenedione, beclomethasone, flumethasone, diflorasone, fluocinolone, clobetasol, cortisone, paramethasone, clocortolone, prednisolone 21-hemisuccinate free acid, prednisolone metasulphobenzoate, prednisolone terbutate, and triamcinolone acetonide 21-palmitate.

By "low dose corticosteroid" is meant a dose that is less than a dose that would typically be given to a patient for treatment of inflammation. Exemplary low doses of corticosteroids are as follows: cortisol: 12 mg/day; cortisone: 15 mg/day; prednisone: 3 mg/day; methylprednisolone: 2.5 mg/day; triamcinolone: 2.5 mg/day; betamethasone: 250 µg/day; dexamethasone: 450 µg/day; hydrocortisone: 9 mg/day.

By a "dosage equivalent to an amoxapine dosage" is meant a dosage of a TCA that, in combination with a given dosage of prednisolone, produces the same anti-inflammatory effect in a patient as a dosage of amoxapine in combination with that dosage of prednisolone.

By a "dosage equivalent to a prednisolone dosage" is meant a dosage of a corticosteroid that, in combination with a given dosage of amoxapine, produces the same anti-inflammatory effect in a patient as a dosage of prednisolone in combination with that dosage of amoxapine.

Other features and advantages of the invention will be apparent from the following detailed description, and from the claims.

DETAILED DESCRIPTION

We have discovered that the combination of amoxapine and prednisolone exhibit substantial TNFα suppressing activity against PBMCs. Concentrations that exhibited effective TNFα suppressing activity were not unacceptably toxic to normal cells. Thus, this drug combination is useful for the treatment of an inflammatory disorder.

Amoxapine

Amoxapine is a tricyclic antidepressant (TCA) of the dibenzoxapine type. It is structurally similar to the older TCAs and also shares similarities with the phenothiazines.

The exact action of TCAs is not fully understood, but it is believed that one of their important effects is the enhancement of the actions of norepinephrine and serotonin by blocking the reuptake of various neurotransmitters at the neuronal membrane. Amoxapine also shares some similarity with antipsychotic drugs in that it blocks dopamine receptors and can cause dyskinesia. Amoxapine also blocks the reuptake of norepinephrine, similar to the action of desipramine and maprotiline.

Based on the ability of amoxapine to act in concert with prednisolone to inhibit TNFα levels, one skilled in the art will recognize that other TCAs, as well as structural and functional analogs of amoxapine, can also be used in combination with prednisolone (or another corticosteroid—see below). Amoxapine analogs include, for example, 8-hydroxyamoxapine, 7-hydroxyamoxapine, loxapine, loxapine succinate, loxapine hydrochloride, 8-hydroxyloxapine, clothiapine, perlapine, fluperlapine, and dibenz (b,f)(1,4)oxazepine, 2-chloro-11-(4-methyl-1-piperazinyl)-, monohydrochloride.

Prednisolone

Prednisolone, a synthetic adrenal corticosteroid, has anti-inflammatory properties, and is used in a wide variety of inflammatory conditions. It is desirable to reduce the amount of administered prednisolone because long-term use of steroids at can produce significant side effects.

Prednisolone is a member of the corticosteroid family of steroids. Based on the shared structural features and apparent mechanism of action among the corticosteroid family, one skilled in the art will recognize that other corticosteroids can be used in combination with amoxapine or an amoxapine analog to treat inflammatory disorders. Corticosteroids include, for example, dexamethasone, betamethasone, triamcinolone, triamcinolone acetonide, triamcinolone diacetate, triamcinolone hexacetonide, beclomethasone, dipropionate, beclomethasone dipropionate monohydrate, flumethasone pivalate, diflorasone diacetate, fluocinolone acetonide, fluorometholone, fluorometholone acetate, clobetasol propionate, desoximethasone, fluoxymesterone, fluprednisolone, hydrocortisone, hydrocortisone acetate, hydrocortisone butyrate, hydrocortisone sodium phosphate, hydrocortisone sodium succinate, hydrocortisone cypionate, hydrocortisone probutate, hydrocortisone valerate, cortisone acetate, paramethasone acetate, methylprednisolone, methylprednisolone acetate, methylprednisolone sodium succinate, prednisolone, prednisolone acetate, prednisolone sodium phosphate, prednisolone tebutate, clocortolone pivalate, flucinolone, dexamethasone 21-acetate, betamethasone 17-valerate, isoflupredone, 9-fluorocortisone, 6-hydroxydexamethasone, dichlorisone, meclorisone, flupredidene, doxibetasol, halopredone, halometasone, clobetasone, diflucortolone, isoflupredone acetate, fluorohydroxyandrostenedione, beclomethasone, flumethasone, diflorasone, fluocinolone, clobetasol, cortisone, paramethasone, clocortolone, prednisolone 21-hemisuccinate free acid, prednisolone metasulphobenzoate, prednisolone terbutate, and triamcinolone acetonide 21-palmitate.

Therapy

Combination therapy according to the invention may be performed alone or in conjunction with another therapy and may be provided at home, the doctor's office, a clinic, a hospital's outpatient department, or a hospital. Treatment generally begins at a hospital so that the doctor can observe the therapy's effects closely and make any adjustments that are needed. The duration of the combination therapy depends on the type of inflammatory disorder being treated, the age and condition of the patient, the stage and type of the patient's disease, and how the patient responds to the treatment. Additionally, a person having a greater risk of developing an inflammatory disorder (e.g., a person who is genetically predisposed or previously had an inflammatory disorder) may receive prophylactic treatment to inhibit or delay an inflammatory response.

The dosage, frequency and mode of administration of each component of the combination can be controlled independently. For example, one compound may be administered orally three times per day, while the second compound may be administered intramuscularly once per day. Combination therapy may be given in on-and-off cycles that include rest periods. The compounds may also be formulated together such that one administration delivers both compounds.

Formulation of Pharmaceutical Compositions

Suitable modes of administration include oral, rectal, intravenous, intramuscular, subcutaneous, inhalation, topical or transdermal, vaginal, and ophthalmic.

The combination of the invention can also be provided as components of a pharmaceutical pack. The two drugs can be formulated together or separately and in individual dosage amounts.

The compounds of the invention are also useful when formulated as salts. For example, amitriptyline, another tricyclic antidepressant, has been formulated as a hydrochloride salt, indicating that amoxapine can be similarly formulated.

Administration of each compound of the combination may be by any suitable means that results in a concentration of the compound that, combined with the other compound, is anti-inflammatory. Each compound is admixed with a suitable carrier substance, and is generally present in an amount of 1–95% by weight of the total weight of the composition. The composition may be provided in a dosage form that is suitable for oral, parenteral (e.g., intravenous, intramuscular, subcutaneous), rectal, transdermal, nasal, vaginal, inhalant, or ocular administration. Thus, the composition may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, or aerosols. The pharmaceutical compositions may be formulated according to conventional pharmaceutical practice (see, e.g., Remington: The Science and Practice of Pharmacy, (19th ed.) ed. A. R. Gennaro, 1995, Mack Publishing Company, Easton, Pa. and Encyclopedia of Pharmaceutical Technology, eds. J. Swarbrick and J. C. Boylan, 1988–1999, Marcel Dekker, N.Y.

Pharmaceutical compositions according to the invention may be formulated to release the active compound substantially immediately upon administration or at any predetermined time period after administration, using controlled release formulations.

Administration of compounds in controlled release formulations is useful where the compound, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes.

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

The two compounds may be mixed together in a tablet or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Dosages

The dosage of each compound of the claimed combinations depends on several factors, including: the administration method, the disease to be treated, the severity of the disease, whether the disease is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect dosage used.

Continuous daily dosing with the combinations of the invention may not be required. A therapeutic regimen may require cycles, during which time a drug is not administered, or therapy may be provided on an as needed basis during periods of acute inflammation.

As described above, the compound in question may be administered orally in the form of tablets, capsules, elixirs or syrups, or rectally in the form of suppositories. Parenteral administration of a compound is suitably performed, for example, in the form of saline solutions or with the compound incorporated into liposomes. In cases where the compound in itself is not sufficiently soluble to be dissolved, a solubilizer such as ethanol can be applied.

Below, for illustrative purposes, the dosages for amoxapine and prednisolone are described. One skilled in the art will readily be able to ascertain suitable dosages for other TCAs and corticosteroids. For example, a TCA can be given in a dosage equivalent to an amoxapine dosage provided below, and a corticosteroid can be given in a dosage equivalent to a predinisolone dosage provided below. In one embodiment, the corticosteroid is a low dose corticosteroid.

Oral Administration

For amoxapine adapted for oral administration for systemic use, the total daily dosage is normally about 1–600 mg (0.01–8.5 mg/kg), preferably about 25–400 mg (0.35–5.7 mg/kg), and more preferably about 100–300 mg (1.4–4.2 mg/kg) total daily dose. Administration can be one to three times daily for one day to one year, and may even be for the life of the patient. Chronic, long-term administration will be indicated in many cases. Daily dosages up to 600 mg may be necessary.

For prednisolone adapted for oral administration for systemic use, the daily dosage is normally about 0.05–200 mg (0.7–2800 mcg/kg), preferably about 0.1–60 mg (1–850 mcg/kg), and more preferably about 0.1–5 mg (4–70 mcg/kg). Because of the enhancing effect exhibited by amoxapine on prednisolone anti-inflammatory activity, low dosages of prednisolone (e.g., 0.2, 0.4, 0.6, 0.8, 1, 2, or 3 mg/day), when combined with a TCA, can be effective in treating inflammation. Administration one to four times daily is desirable. Like amoxapine, prednisilone may be administered for one day to one year, and may even be for the life of the patient. Dosages up to 200 mg per day may be necessary.

Rectal Administration

For compositions adapted for rectal use for preventing disease, a somewhat higher amount of a compound is usually preferred. Thus a total daily dosage of amoxapine is normally about 1–600 mg (0.01–8.5 mg/kg). Rectal administration of amoxapine is normally one to three times daily. A total daily dosage of prednisolone is normally about 0.1–100 mg (1–1420 mcg/kg). Rectal administration of prednisolone is normally one to four times daily.

Intravenous Administration

For intravenous administration of amoxapine, a total daily dosage is about 1–400 mg (0.014–5.7 mg/kg), preferably about 10–200 mg (0.14–2.8 mg/kg) and more preferably about 25–100 mg (0.35–1.4 mg/kg). Intravenous administration of amoxapine is normally one to four times daily, but can be continuously infused.

For intravenous administration of prednisolone, a total daily dosage is about 0.05–200 mg (0.0007–2.8 mg/kg), preferably about 0.1–60 mg (0.001–0.85 mg/kg), and more preferably about 0.1–5 mg (4–70 mcg/kg). Low dosages of prednisolone, described above, are most preferred. Intravenous administration of prednisolone is normally one to four times daily, but, like amoxapine, can be continuously infused.

Additional Routes of Administration

For intramuscular, subcutaneous, inhalation, topical, vaginal, or ophthalmic administration of amoxapine, a total daily dosage is about 1–400 mg (0.014–5.7 mg/kg), preferably about 10–200 mg (0.14–2.8 mg/kg), and more preferably about 25–100 mg (0.35–1.4 mg/kg), and a total daily dosage of prednisolone is about 0.1–100 mg (0.0014–1.42 mg/kg). By these routes, administration of each of amoxapine and prednisolone is, independently, one to four times daily.

The following examples are to illustrate the invention. They are not meant to limit the invention in any way.

EXAMPLE 1

Preparation of Pairwise Compound Mixed Combination Serial Dilution Matrix

Stock solutions of amoxapine (16 mg/ml) (Sigma-Aldrich, St. Louis, Mo.; catalog number A129) and prednisolone (1.6 mg/ml) (Sigma-Aldrich, catalog number P6004) were made in dimethylsulfoxide (DMSO). The amoxapine master plates were made by adding 25 µl of the concentrated stock solution to columns 3, 9, and 15 (rows C through N) of a polypropylene 384-well storage plate that had been pre-filled with 75 µl of anhydrous DMSO. Using a TomTec Quadra Plus liquid handler, the 25 µl of amoxapine stock solution was serially diluted two-fold four times into the adjacent columns (columns 4–7, 10–13, 16–19). The sixth column (8, 14, and 20) did not receive any compound and served as a vehicle control. The prednisolone master plates were made by adding 25 µl of the concentrated prednisolone stock solution to the appropriate wells (row C, columns 3–8; row C, columns 9–14; row C, columns 15–20; row I, columns 3–8; row I, columns 9–14; row I, columns 15–20) of the appropriate prednisolone master polypropylene 384-well storage plate. These master plates had been pre-filled with 75 µl of anhydrous DMSO. Using the TomTec Quadra Plus liquid handler, the 25 µl was serially diluted two-fold four times in the adjacent rows (rows D–G, and J–M). The sixth row (H and N) did not receive any compound to serve as a vehicle control. Master plates were sealed and stored at −20° C. until ready for use.

The final amoxapine/prednisolone combination plate was generated by transferring 1 µl from each of the amoxapine and prednisolone master plates to a dilution plate containing 100 µl of media (RPMI; Gibco BRL, #11875-085), 10% Fetal Bovine Serum (Gibco BRL, #25140-097), 2% Penicillin/Streptomycin (Gibco BRL, #15140-122)) using the TomTec Quadra Plus liquid handler. This dilution plate was then mixed and a 10 µl aliquot transferred to the final assay plate, which had been pre-filled with 40 µl/well RPMI media containing the appropriate stimulant to activate TNFα secretion (see below).

EXAMPLE 2

Assay for TNFα Suppressing Activity of Amoxapine and Prednisolone

The compound dilution matrix was assayed using a TNFα ELISA method. Briefly, a 100 µl suspension of diluted human peripheral blood mononuclear cells (PBMCs) contained within each well of a polystyrene 384-well plate (NalgeNunc) was stimulated to secrete TNFα by treatment with a final concentration of 10 ng/ml phorbol 12-myristate 13-acetate (Sigma) and 750 ng/µl ionomycin (Sigma). Various concentrations of each test compound were added at the time of stimulation. After 16–18 hours of incubation at 37° C. in a humidified incubator, the plate was centrifuged and the supernatant transferred to a white opaque polystyrene 384 well plate (NalgeNunc, Maxisorb) coated with an anti-TNF antibody (PharMingen, #18631D). After a two-hour incubation, the plate was washed (Tecan PowerWasher 384) with phosphate buffered saline (PBS) containing 0.1 % Tween 20 (polyoxyethylene sorbitan monolaurate) and incubated for an additional one hour with another anti-TNF antibody that was biotin labeled (PharMingen, 18642D) and horseradish peroxidase (HRP) coupled to strepavidin (PharMingen, #13047E). After the plate was washed with 0.1% Tween 20/PBS, the HRP substrate (which contains luminol, hydrogen peroxide, and an enhancer such as para-iodophenol) was added to each well and light intensity measured using a LJL Analyst luminometer. Control wells contained a final concentration of 1 µg/ml cyclosporin A (Sigma).

EXAMPLE 3

Suppression of TNFα Secretion from Phorbol 12-myristate 13-acetate and Ionomycin Treated Blood by a Combination of Amoxapine and Prednisolone Together, amoxapine and prednisolone were able to suppress phorbol 12-myristate 13-acetate and ionomycin induced TNFα secretion in blood. As is shown in Tables 1 and 2, amoxapine is able to enhance the dose response of prednisolone by nearly two fold. At a concentration of 1.11 µM, prednisolone alone is able to inhibit TNFα secretion by 28%. Addition of 0.2 µM amoxapine increases the TNFα inhibition of the 1.11 µM prednisolone to 51%. This large increase in activity of 82% is created by a relatively small increase of only 18% in total drug species.

TABLE 1

| Prednisolone [µM] | Amoxapine [µM] | | | | | |
|---|---|---|---|---|---|---|
| | 12.750 | 3.188 | 0.797 | 0.199 | 0.050 | 0.000 |
| 1.110 | 85.89 | 66.47 | 47.73 | 50.93 | 32.79 | 27.59 |
| 0.277 | 82.82 | 58.88 | 48.79 | 34.40 | 29.17 | 26.81 |
| 0.069 | 78.58 | 60.66 | 41.32 | 34.99 | 21.41 | 22.31 |
| 0.017 | 84.69 | 62.66 | 34.66 | 32.48 | 21.39 | 19.06 |
| 0.004 | 84.13 | 53.41 | 33.86 | 16.02 | 5.82 | 2.69 |
| 0.000 | 73.02 | 50.44 | 24.29 | 16.66 | 7.30 | 0.00 |

TABLE 2

| Prednisilone [µM] | Amoxapine [µM] | | | | | | | | | |
|---|---|---|---|---|---|---|---|---|---|---|
| | 12.747 | 6.373 | 3.187 | 1.593 | 0.797 | 0.398 | 0.199 | 0.100 | 0.050 | 0.000 |
| 1.110 | 88.35 | 74.63 | 66.76 | 65.79 | 57.72 | 52.50 | 45.50 | 43.72 | 40.04 | 34.62 |
| 0.555 | 90.09 | 76.42 | 69.66 | 60.08 | 53.51 | 46.73 | 41.70 | 43.67 | 31.76 | 30.50 |
| 0.277 | 86.67 | 75.34 | 66.45 | 59.64 | 54.23 | 46.97 | 45.38 | 35.20 | 34.42 | 36.89 |
| 0.139 | 91.50 | 78.45 | 70.37 | 60.75 | 54.73 | 47.05 | 41.51 | 37.79 | 28.46 | 25.74 |
| 0.069 | 36.59 | 86.03 | 77.74 | 67.81 | 57.14 | 49.96 | 37.24 | 33.39 | 31.75 | 24.56 |
| 0.035 | 92.76 | 80.28 | 70.42 | 59.40 | 52.58 | 47.40 | 37.94 | 34.59 | 21.47 | 24.06 |
| 0.017 | 91.02 | 75.16 | 72.06 | 56.40 | 45.14 | 47.84 | 36.50 | 24.33 | 21.92 | 24.74 |
| 0.009 | 88.58 | 72.16 | 71.61 | 56.03 | 49.80 | 39.87 | 28.66 | 27.23 | 17.78 | 14.34 |
| 0.004 | 84.32 | 66.14 | 57.21 | 46.53 | 32.06 | 27.76 | 23.73 | 15.94 | 12.99 | 9.62 |
| 0.000 | 80.89 | 64.40 | 47.96 | 37.13 | 21.88 | 16.38 | 14.19 | 3.60 | −3.31 | −0.97 |

Amoxapine enhancement of prednisolone activity was also observed in a follow-up secondary screen. The TNFα inhibition of prednisolone at a concentration of 9 nM was increased 2.9 fold to 40% in the presence of 400 nM amoxapine. The TNFα inhibition activity of prednisolone and amoxapine alone at these concentrations is only 14 and 16% respectively. Moreover, the level of TNFα inhibition achieved by 9 nM prednisolone in combination with 398 nM amoxapine (40%) is no less than that of 1110 nM prednisolone alone (35%). This increase in TNFα inhibition constitutes a potency shift of as much as 100-fold for the combination, compared to prednisolone alone.

The ability of amoxapine and prednisolone to inhibit TNFα secretion from LPS stimulated blood is shown in Table 3.

TABLE 3

| Prednisolone [μM] | Amoxapine [μM] | | | | | | | | | |
|---|---|---|---|---|---|---|---|---|---|---|
| | 12.747 | 6.373 | 3.187 | 1.593 | 0.797 | 0.398 | 0.199 | 0.100 | 0.050 | 0.000 |
| 1.110 | 78.97 | 71.52 | 67.84 | 63.65 | 66.04 | 68.04 | 61.29 | 64.30 | 58.19 | 60.06 |
| 0.555 | 83.61 | 68.05 | 62.72 | 65.82 | 59.46 | 56.17 | 56.36 | 55.47 | 55.94 | 47.15 |
| 0.277 | 70.40 | 64.01 | 62.08 | 57.91 | 55.42 | 54.64 | 56.94 | 51.39 | 50.05 | 48.75 |
| 0.139 | 72.56 | 60.77 | 58.36 | 55.47 | 50.42 | 49.25 | 49.54 | 48.74 | 44.46 | 48.46 |
| 0.069 | 70.27 | 73.99 | 61.88 | 48.82 | 43.56 | 47.22 | 42.13 | 42.62 | 44.19 | 38.79 |
| 0.035 | 86.37 | 64.17 | 43.28 | 38.16 | 37.26 | 37.96 | 38.06 | 40.83 | 32.87 | 33.11 |
| 0.017 | 78.81 | 48.94 | 42.94 | 40.81 | 37.94 | 35.96 | 32.00 | 35.25 | 29.35 | 37.12 |
| 0.009 | 67.09 | 43.76 | 41.07 | 34.23 | 25.54 | 24.86 | 31.12 | 23.57 | 27.36 | 30.24 |
| 0.004 | 60.14 | 37.59 | 34.03 | 25.52 | 24.94 | 27.78 | 25.57 | 30.40 | 18.90 | 12.06 |
| 0.000 | 49.64 | 21.26 | 24.21 | 16.79 | 13.11 | 8.10 | 2.39 | 5.52 | 3.00 | −1.31 |

OTHER EMBODIMENTS

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology or related fields are intended to be within the scope of the invention.

What is claimed is:

1. A pharmaceutical composition formulated for oral, rectal, intravenous, intramuscular, subcutaneous, inhalation, vaginal, or ophthalmic administration, said composition comprising amoxapine and a corticosteroid, wherein the amoxapine and corticosteroid are present in amounts that, when administered together to a patient having an inflammatory disorder, inhibit or reduce inflammation.

2. The composition of claim 1, wherein amoxapine is present in the composition in an amount of 1–600 milligrams.

3. The composition of claim 2, wherein amoxapine is present in the composition in an amount of 100–300 milligrams.

4. The composition of claim 1, wherein the steroid is present in the composition in an amount of 0.05–200 milligrams.

5. The composition of claim 4, wherein the steroid is present in the composition in an amount of 0.05–5 milligrams.

6. The composition of claim 5, wherein the steroid is present in the composition in an amount of 0.1–3 milligrams.

7. The composition of claim 1, wherein the composition is formulated for oral administration.

8. The composition of claim 1, wherein the composition is formulated for rectal administration.

* * * * *